United States Patent

Djang

(10) Patent No.: US 8,584,292 B1
(45) Date of Patent: Nov. 19, 2013

(54) DUAL ROTATING ELECTRIC TOOTHBRUSH

(76) Inventor: Sam Djang, North Hills, CA (US)

( * ) Notice: Subject to any disclaimer, the term of this patent is extended or adjusted under 35 U.S.C. 154(b) by 186 days.

(21) Appl. No.: 13/373,817

(22) Filed: Dec. 1, 2011

Related U.S. Application Data

(63) Continuation-in-part of application No. 11/850,388, filed on Sep. 5, 2007, now abandoned.

(51) Int. Cl.
*A61C 17/26* (2006.01)

(52) U.S. Cl.
USPC .................................................. 15/23

(58) Field of Classification Search
USPC .................................................. 15/23
See application file for complete search history.

(56) References Cited

U.S. PATENT DOCUMENTS

| | | | | |
|---|---|---|---|---|
| 2,124,145 A | * | 7/1938 | Merkel, Jr. | 15/23 |
| 2,583,886 A | * | 1/1952 | Schlegel | 15/23 |
| 2,628,377 A | | 2/1953 | Cochriel | |
| 2,655,675 A | * | 10/1953 | Grover | 15/23 |
| 2,739,327 A | * | 3/1956 | Blair | 15/23 |
| 2,758,326 A | | 8/1956 | Keely et al. | |
| 3,258,802 A | * | 7/1966 | Rodriguez | 15/23 |
| 3,800,350 A | * | 4/1974 | Francolino | 15/23 |
| 4,313,237 A | | 2/1982 | Smith | |
| 4,603,448 A | * | 8/1986 | Middleton et al. | 15/22.1 |
| 5,027,463 A | | 7/1991 | Daub | |
| 5,177,827 A | | 1/1993 | Ellison | |
| 5,864,911 A | | 2/1999 | Arnoux et al. | |
| 6,625,834 B2 | | 9/2003 | Dean | |

FOREIGN PATENT DOCUMENTS

| | | | |
|---|---|---|---|
| DE | 19805770 | * | 8/1998 |
| EP | 488971 | * | 6/1992 |
| FR | 2662598 | * | 12/1991 |
| WO | 02/096314 | * | 12/2002 |
| WO | 2006/006808 | * | 1/2006 |

* cited by examiner

*Primary Examiner* — Mark Spisich
(74) *Attorney, Agent, or Firm* — Albert O. Cota

(57) ABSTRACT

A powered, mechanical teeth cleaning device having a pair of rotating brushes. The brushes rotate inward from each side, providing a cleaning effect on both buccal and lingual surfaces of a tooth from the gum tissue to the tooth. The toothbrush automatically adjusts the pressure applied to the pair of brushes in response to the width of a particular interfacing tooth. The toothbrush also has protective shield for minimizing mouth tissue irritation, and a guiding stop for proper tooth positioning.

15 Claims, 18 Drawing Sheets

DUAL ROTATING ELECTRIC TOOTHBRUSH

This application is a Continuation-In-Part (CIP) of application Ser. No. 11/850,388 filed Sep. 5, 2007 now abandoned.

TECHNICAL FIELD

The invention generally pertains to electrically driven teeth cleaning devices, and more particularly to a dual rotating electric toothbrush that automatically adjusts the pressure applied to the teeth.

BACKGROUND ART

For a long time specialists have agreed that in order to be effective, teeth must be brushed from the gum towards the end of the tooth, i.e, downwards for the top jaw and upwards for the bottom jaw.

It has been a long standing need to make a perfect tooth cleaning device. Most dental decay and gum problems start from the area called embrasure, which is the space located between two adjacent teeth and the gum line. Present manual and electrical toothbrushes can not reach these areas very efficiently. In addition, brushing direction is important to protect the gum line from receding. To achieve this goal, the brushing direction should be on the long axis of the tooth and at the same time, it should be directed from the gum tissue towards the direction of the target tooth. In the present market, there are some toothbrushes manufactured based on this concept. However, since the designers of these toothbrushes apparently ignored major or minor structural parts or system in their designs, their products can lead to one or more secondary problems or can never reach the intended goal.

A search of the prior art did not disclose any literature or patents that read directly on the claims of the instant invention. However, the following U.S. patents are considered related.

| PAT. NO. | INVENTOR | ISSUED |
| --- | --- | --- |
| 6,625,834 | Dean | 30 Sep. 2003 |
| 5,864,911 | Arnoux et al | 2 Feb. 1999 |
| 5,177,827 | Ellison | 12 Jan. 1993 |
| 5,027,463 | Daub | 2 Jul. 1991 |
| 4,313,237 | Smith | 2 Feb. 1982 |
| 2,758,326 | Keely et al | 14 Aug. 1956 |
| 2,628,377 | Cochriel | 17 Feb. 1953 |

The U.S. Pat. No. 6,625,834 discloses a preferably non-electric, non-mechanically actuated toothbrush having a generally U-shaped appearance with a rotary brush located, during use, on each side of a tooth to be cleaned. The brushes are configured to rotate about an axis which is parallel to the long axis of the tooth to be cleaned, and essentially perpendicular to the buccal and lingual gum line, of the user. The brushes are preferably held in contact with the teeth and gum tissue by a resilient section of the toothbrush. In this fashion, a pushing and pulling motion during brushing results in a rotational motion of the brushes.

The U.S. Pat. No. 5,864,911 discloses a mechanical toothbrush with a dual rotary brushing system and comprising a handle-forming body and a head fixed to the handle which is provided with two adjacent contra-rotating brushes of cylindrical shape and having substantially parallel axes. Each of the two brushes is driven by a flexible shaft situated in the head and supported, at least at its distal end, by a respective bearing mounted on a support that enables the two brushes to move apart, one away from the other, then urging the brushes towards the other by a return effect.

The U.S. Pat. No. 5,177,827 discloses a simplified single-procedure approach to self-administered dental-care, achieved through means of a special hand-portable/battery-powered instrument, having a chargeable-battery and a motor with gear-reduction contained within the handle portion. While preferably detachably-mounted thereto is a special extensile bifurcated structure provided with lateral adjustability by which to accommodate variations in individual mouth width, while supporting a plurality of motor-drive rotary-brush elements capable of uniformly scrubbing all of the mouth's teeth, away from the gums, inside and out, in a simultaneous single motion fully-automated manner. Hence, the notion of a manually inserted, selectively actuated oral instrument, serving to brush clean the entire inside mouth surfaces of the gums, teeth, and adjoining cheek and tongue surfaces in a rapid simultaneous manner being a substantial advancement, efficiently eliminating reliance upon one's own manual dexterity for effectual daily oral-hygiene.

The U.S. Pat. No. 5,027,463 discloses a toothbrush for use in simultaneously brushing and cleaning the occlusal, lingual and buccal surfaces of the upper and lower teeth of a user. The toothbrush, in the preferred embodiment, is power-driven and includes bristle support member which anchors bristles from opposite surfaces thereof. The bristles are arranged in longitudinal rows including central rows, intermediate rows and outer rows. The central rows are straight while the intermediate and outer rows are curved for engaging the lingual and buccal surfaces. The bristles are shaped and arranged in a heating chamber while being anchored to the bristle support member.

The U.S. Pat. No. 4,313,237 discloses an improved driven rotary toothbrush having an electric motor enclosed in a handle and driving a plurality of rotary brushes for simultaneously cleaning multiple tooth surfaces. The rotary brushes are mounted in a brush head adapted to be releasably supported on one end of an elongated brush head support stem having flexible drive shafts extending therealong and having its other end adapted to be releasably mounted on the handle to provide rotary driven connection between the motor and brushes. The releasable mounting of the brush head and of the support stem enables hygienic use of the same motor and handle by a plurality of persons through use of personalized snap-on brush heads and support stems, and also makes possible the easy and economical replacement of the brush heads.

The U.S. Pat. No. 2,758,326 discloses a power driven rotary toothbrush which enables the user to reach without difficulty the teeth least accessible, i.e., the back molars, and which subjects the teeth to gentle yet effective and approved cleaning action.

The U.S. Pat. No. 2,628,377 discloses a mechanical toothbrush having rotary brushes.

While these patents and other previous methods have attempted to solve the problems that they addressed, none have utilized or disclosed a protective shield directed to addressing soft tissue irritation, oral cavity malignancies and splashing, and/or a guiding stop directed to proper tooth positioning of the device, as does embodiments of the technology described herein.

Therefore, a need exists for a dual rotating electric toothbrush with these attributes and functionalities. The dual rotating electric toothbrush according to embodiments of the invention substantially departs from the conventional concepts and designs of the prior art. It can be appreciated that there exists a continuing need for a new and improved dual rotating electric toothbrush which can be used commercially. In this regard, the technology described herein substantially fulfills these objectives.

The foregoing patent and other information reflect the state of the art of which the inventor is aware and are tendered with a view toward discharging the inventor's acknowledged duty of candor in disclosing information that may be pertinent to the patentability of the technology described herein. It is respectfully stipulated, however, that the foregoing application and other information do not each or render obvious, singly or when considered in combination, the inventor's claimed invention.

DISCLOSURE OF THE INVENTION

The technology described herein is directed to a dual rotating electric toothbrush having two lines of electrically powered rotating brushes, i.e., bristles, which protrude from the handle. The bristles rotate inward from each side, giving a brushing effect on both buccal and lingual surfaces of the tooth from the gum tissue to the tooth direction. Ideal brushing direction should be on the long axis of the tooth, at the same time it should be from the gum tissue to the tooth direction. In this manner, the most critical area in the tooth brushing, that is the embrasure between two adjacent teeth and the gum line, can be cleaned more effectively and at the same time gum tissue, or gingival, can be saved from detachment or receding.

The applicant's technology is directed to having:

1. Electrical sensors that direct tooth width automatically adjusts the brushes for the width of the teeth.
2. A version adapted for pets and animals.
3. A version adapted for children, teens, adults and elderly persons.

The technology described herein has two lines of electrically driven rotating bristles, which project outward and longitudinally from the body of the brush. When the user places and seats the head tip of the brush with two parallel lines of wire with the bristles onto the occlusal or incisal surface of the tooth, each of the bristle lines cover both the buccal and the lingual surfaces of the tooth respectively. The bristles then rotate inward from each side, giving a brushing effect on both the buccal and the lingual surfaces of the tooth vertically from the gum tissue to the tooth direction. Unlike other similar designs, e.g., U.S. Pat. No. 5,864,911, there is a space or a gap between the two lines of the bristles, which guides the user to position the toothbrush correctly.

Different combinations of spacing and arrangement of the dual head can make a significant difference for a user. Since each tooth has different dimensional thickness or width, the user is advised to slidably move the toothbrush in a buccolingual direction. The user can also push the switch on the body of the brush to the front teeth side to make the two lines of bristles move inward, so that they cover the bucco-lingually narrowed front teeth.

The technology described herein has a dual head supporting system and a covering which other designs, such as U.S. Pat. No. 5,864,911 lack. Without this covering, the user will suffer irritation of the soft tissue including the inner wall of the cheek and lips. This repeated irritation can cause not only injury to the oral soft tissue but also cause malignancies in the oral cavity.

One advantage of the technology described herein is that the covering works as a protective shield to stop or minimize the splashing out of saliva and/or toothpaste from a user's mouth.

Another advantage of the technology described herein is a guiding stop, located at the most middle part of the head tip of the brush. This stop guides the user to the correct position for a tooth. Without this stop, the user has more chances of making a mistake in positioning the brush with or without being in front of a mirror.

Another advantage of the technology described herein is that it is made economically.

Another advantage of the technology described herein is that it is made from readily available materials.

These and other objects and advantages of the present invention will become apparent from the subsequent detailed description of the preferred embodiment and the appended claims taken in conjunction with the accompanying drawings.

BRIEF DESCRIPTION OF THE DRAWINGS

The invention, together with further advantages thereof, may best be understood by reference to the following description of the invention, taken in conjunction with the accompanying drawings in which.

BEST MODE FOR CARRYING OUT THE INVENTION

The technology described herein will now be described in detail with reference to at least one preferred embodiment thereof as illustrated in the accompanying drawings. In the following description, numerous specific details are set forth in order to provide a thorough understanding of the technology described herein. It will be apparent, however, to one skilled in the art, that the technology described herein may be practiced without some or all of these specific details. In other instances, well known operations have not been described in detail so not to unnecessarily obscure the technology described herein.

Figure 1:
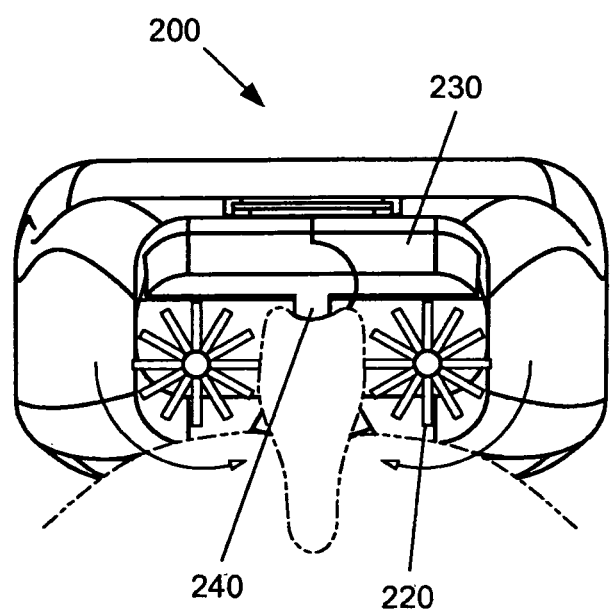
FIG. 1 is a front elevational view of a head assembly with the guiding stop in a horizontal position.
Figure 2:
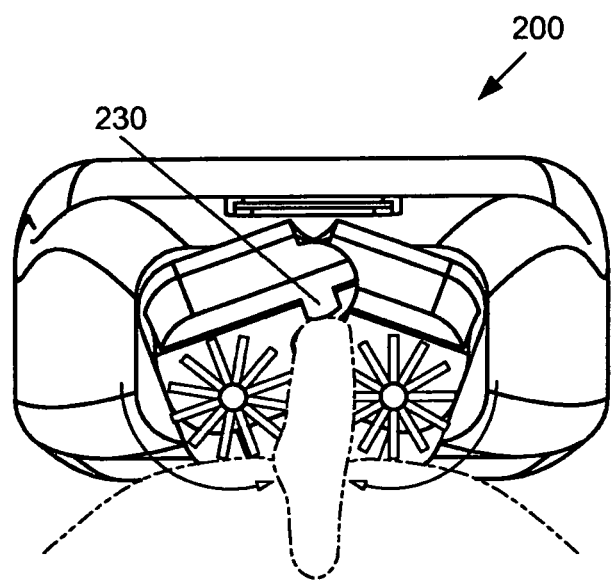
FIG. 2 is a front elevational view of a head assembly with the guiding stop in a non-horizontal position.
Figure 3:
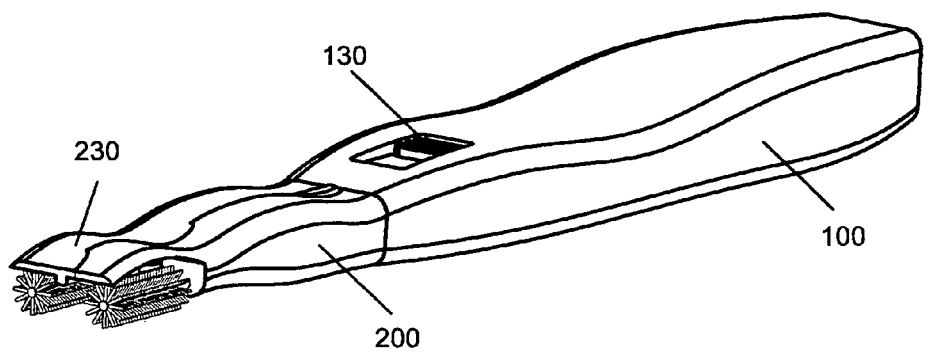
FIG. 3 is a top perspective view of a dual rotating electric toothbrush.
Figure 4:
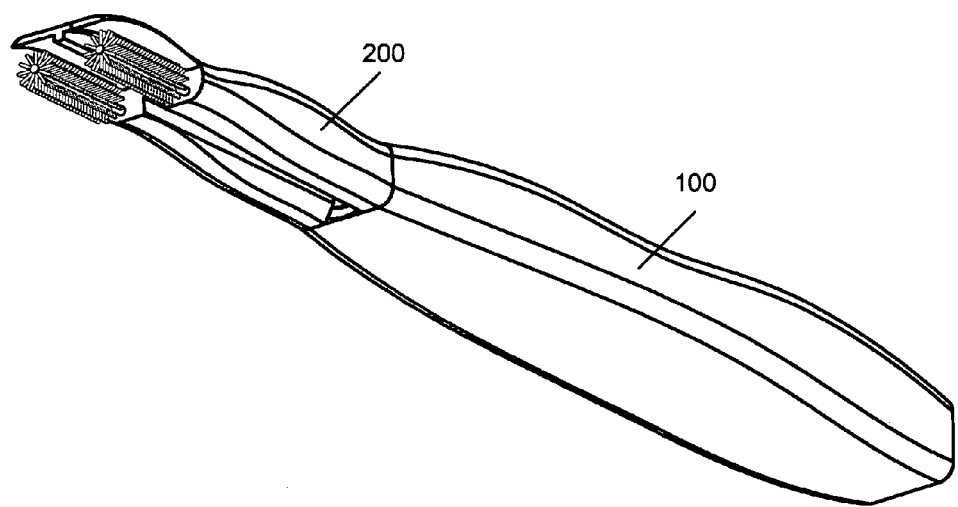
FIG. 4 is a bottom perspective view of a dual rotating electric toothbrush.
Figure 5:
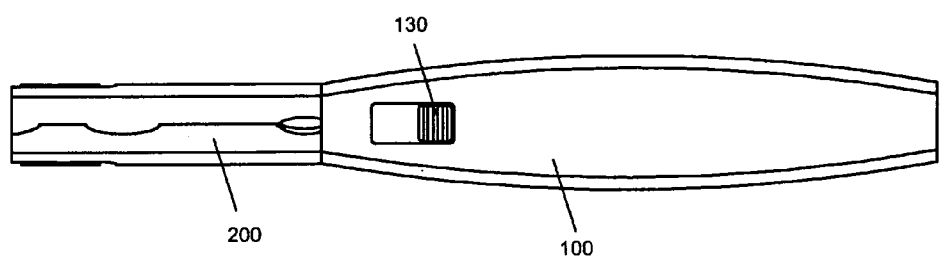
FIG. 5 is a top elevational view of a dual rotating electric toothbrush.
Figure 6:
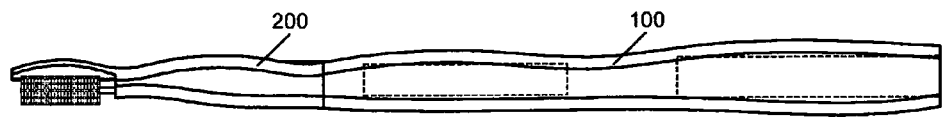
FIG. 6 is a side plan view of a dual rotating electric toothbrush.
Figure 7:
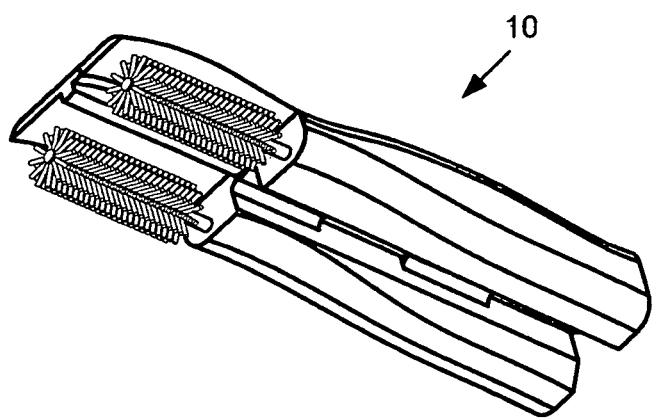
FIG. 7 is a bottom perspective view of a dual rotating electric toothbrush.
Figure 8:
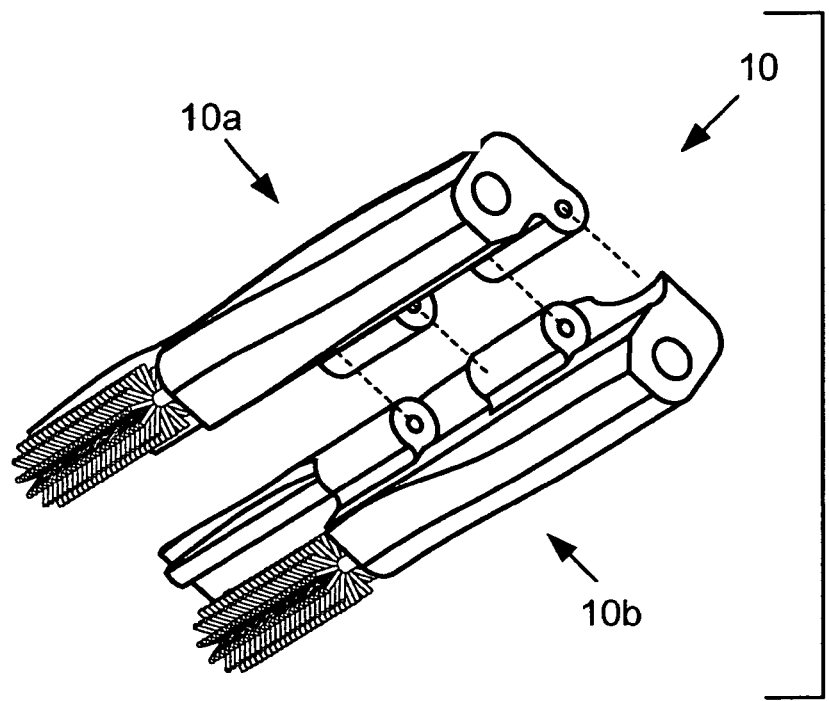
FIG. 8 is a bottom exploded view of a dual rotating electric toothbrush.
Figure 9:
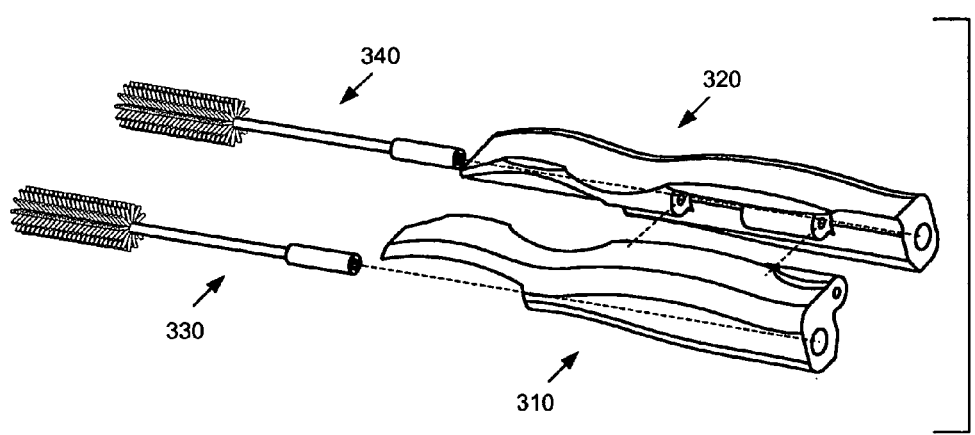
FIG. 9 is a top exploded view of a dual rotating electric toothbrush.
Figure 10:
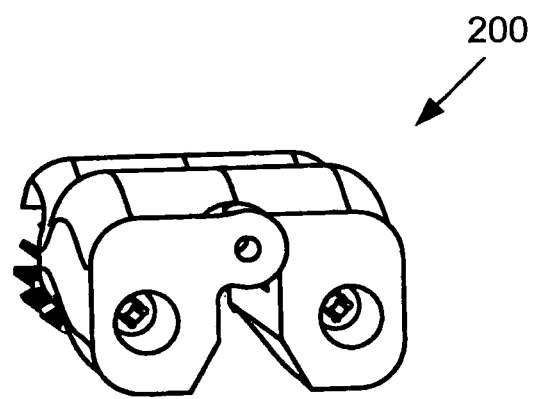
FIG. 10 is a rear perspective view of a dual rotating electric toothbrush.
Figure 11:
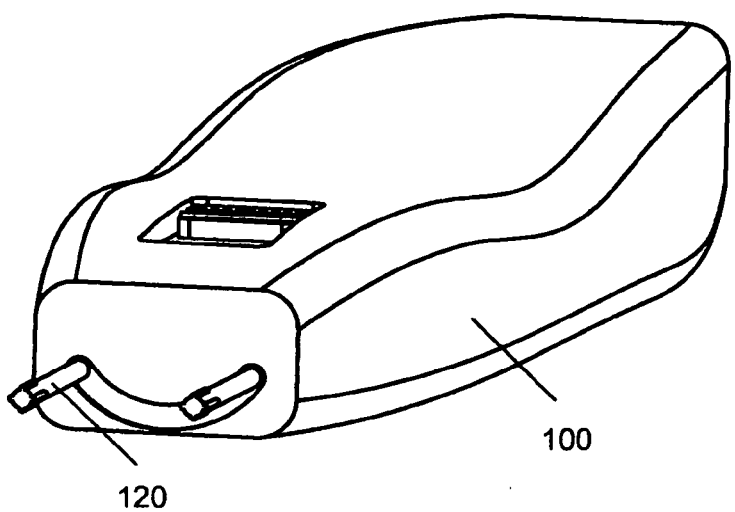
FIG. 11 is a front perspective view of a dual rotating electric toothbrush.
Figure 12:
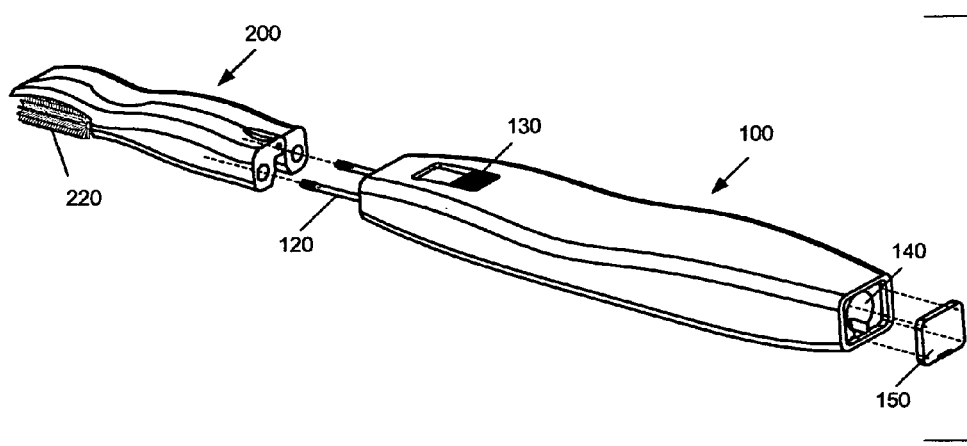
FIG. 12 is a back exploded view of a dual rotating electric toothbrush
Figure 13:
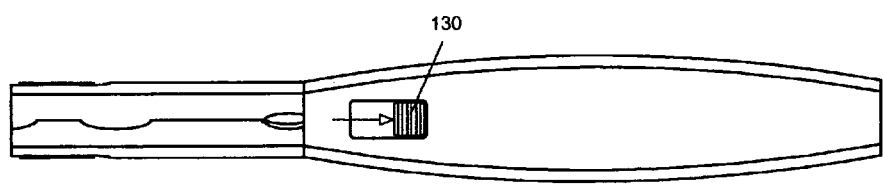
FIG. 13 is a top plan view of a dual rotating electric toothbrush with the bristle direction switch placed in a first position.
Figure 14:
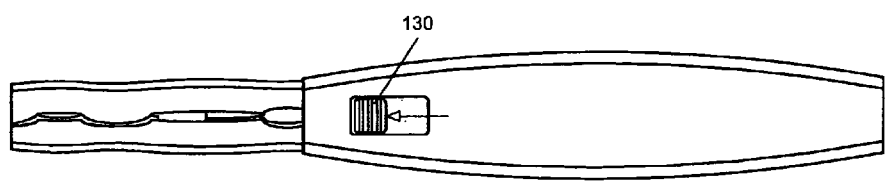
FIG. 14 is a top plan view of a dual rotating electric toothbrush with the bristle direction switch placed in a second position.

Referring to FIGS. 1-19, like reference numerals designate corresponding parts throughout the figures, reference is made first to FIG. 1 which illustrates a head assembly 200.

The dual rotating electric toothbrush is comprised of a body assembly 100 and a head assembly 200. In an exemplary embodiment the length of the body assembly 100 ranges from 6-7 inches, is 0.75 inches thick and has a 1.5 inch diameter oval shaped structure. The body assembly is further comprised of a motor and a battery chamber 140 and battery chamber closure 150. At the front end of the body assembly 100 are located two 0.5 inch long cylinders 120 that extend outward and, which function as male parts when a user connects the head assembly 200 to the body assembly 100.

The head assembly 200 is about 3 inches long with about one inch of this being the head tip. The head assembly 200 is connected to the body assembly 100 with a simple snap-in motion. The head tip has an open area where two lines of bristles 220 are fixed to the wires or cylinders. The wires or cylinders are connected to a power source for rotation, once the switch 130 is positioned to complete the circuit. The wires or cylinders are flexible so that they can adjust to embrace different dimensions of the teeth. The dimensions of the head tip are about 0.75 inch wide from a dorsal point of view and about 0.5 inch height from a side view. Between the two lines of bristles there is about a 0.125 inch gap or space.

A head cover 230 covers the upper portion of the bristles 220 in order to protect the inner cheeks or lips of the user from unpleasant feelings or mechanical injury. At the tip of the brush head, in the middle of the two lines of bristles 220, there is a prominent feature which works as a guiding stop 240. With this guiding stop 240, a user has a higher probability of positioning the bristles 220 correctly. From the ventral view of the head assembly there is an opening not only for the 1.0 inch long head tip portion where actual brushing actions are performed but also for the second part of the head assembly 200, which is about 2.0 inches long, 0.5 inches wide and 1.75 inches in length. This space provides accommodation of the dentition for the user to position the brush tip in as correct of a position as possible. This feature makes it possible to position the bristle line close to perpendicular to the long axis of a tooth.

In a second embodiment of the technology described herein, a cylindrical dual rotating electric toothbrush 10 is comprised of a left brush assembly 10a and a right brush assembly 10b. Each of these assemblies has a battery chamber, battery chamber closure, brush activation switch and corresponding circuitry. The left brush assembly 10a is comprised of a left body element 310 and a left brush element 330. The right brush assembly 10b is comprised of a right body element 320 and a right brush element 340.

The technology described herein may also be described as follows:

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to accommodate the dentition;

a guiding stop located at a center, underside position of the head tip, configured to aid a user in obtaining a correct dentition placement position of the head tip and the brushes on one or more teeth; and a cover portion on the head tip to provide a shielding protection between the rotating brushes and a cheek, tongue, or lip of a user, thereby preventing discomfort or injury to the user.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition; and a guiding stop located at a center, underside position of the head tip, configured to aid a user in obtaining a correct dentition placement position of the head tip and the brushes on one or more teeth; where the head tip is hingedly divisible at a pivot-point location on an underside of the guiding stop, thereby narrowing the gap between the rotating brushes configured to correctly accommodate the dentition and thereby accommodating narrow or front teeth.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition;

a guiding stop located at a center, underside position of the head tip, configured to aid a user in obtaining a correct dentition placement position of the head tip and the brushes on one or more teeth;

a cover portion on the head tip to provide a shielding protection between the rotating brushes and a cheek, tongue, or lip of a user, thereby preventing discomfort or injury to the user; and a toggle switch located on the body of the mechanical teeth-cleaning device, the toggle switch configured to change between two predetermined width settings, thereby changing a width of the gap configured to correctly accommodate the dentition, wherein the toggle switch is configured to switch between two settings: one representing a width of front teeth and one representing a width of back teeth.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition;

a guiding stop located at a center, underside position of the head tip, configured to aid a user in obtaining a correct dentition placement position of the head tip and the brushes on one or more teeth; and a cover portion on the head tip to provide a shielding protection between the rotating brushes and a cheek, tongue, or lip of a user, thereby preventing discomfort or injury to the user; wherein the motor of the mechanical teeth-cleaning device is configured to utilize and derive power from both an AC voltage source and a DC voltage source interchangeably.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition;

a guiding stop located at a center, underside position of the head tip, configured to aid a user in obtaining a correct dentition placement position of the head tip and the brushes on one or more teeth; and a cover portion on the head tip to provide a shielding protection between the rotating brushes and a cheek, tongue, or lip of a user, thereby preventing discomfort or injury to the user; where the two, generally parallel, rotating brushes located in the head tip are configured to rotate in a direction from a gum area upward to a tooth area on a long axis of the tooth to address cleaning an embrasure located between two adjacent teeth and a gum line, and where the rotating brushes are configured to prevent gingival from detachment or retrocession.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition;

a guiding stop located at a center, underside position of the head tip, configured to aid a user in obtaining a correct dentition placement position of the head tip and the brushes on one or more teeth;

a cover portion on the head tip to provide a shielding protection between the rotating brushes and a cheek, tongue, or lip of a user, thereby preventing discomfort or injury to the user; and one or more electrical sensors configured to automatically detect a width of one or more teeth and to automatically and continually adjust a width of the gap between the rotating brushes configured to correctly accommodate the dentition.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition;

a guiding stop located at a center, underside position of the head tip, configured to aid a user in obtaining a correct dentition placement position of the head tip and the brushes on one or more teeth; and a cover portion on the head tip to provide a shielding protection between the rotating brushes and a cheek, tongue, or lip of a user, thereby preventing discomfort or injury to the user; where the rotating brushes further comprise bristles of varying lengths and diameters.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition;

a guiding stop located at a center, underside position of the head tip, configured to aid a user in obtaining a correct dentition placement position of the head tip and the brushes on one or more teeth; and a cover portion on the head tip to provide a shielding protection between the rotating brushes and a cheek, tongue, or lip of a user, thereby preventing discomfort or injury to the user; thereby preventing discomfort or injury to the user, wherein the cylindrical, rotatable shafts are comprised of a flexible material to bend as necessary to accommodate varying sizes of teeth.

A mechanical teeth-cleaning device having two motorized lines of rotating brushes, the device comprising:

a body defining a user handle, the body contoured to provide gripability, the body configured to contain a miniaturized motor to provide two shafts with counter-rotation and a battery chamber, the body having two protruding and substantially parallel, cylindrical, rotatable shafts mechanically coupled to the motor and configured to provide rotation each in a direction opposite to one another;

a head secured to the body, configured to connect to the body with a snap-in motion and mechanically coupled to the cylindrical, rotatable shafts;

a head tip containing two, generally parallel, rotating brushes exposed on their sides and undersides, the head tip located at the top of the head, each rotating brush being generally cylindrical and each connecting to one of the cylindrical, rotatable shafts, the rotating brushes configured for simultaneous contact with dentition, one with a buccal side and the other with a lingual side, and each rotating brush being separated one from another by a gap of a predetermined width and configured to correctly accommodate the dentition;

a guiding stop located at a center, underside position of the head tip, configured to aid a user in obtaining a correct dentition placement position of the head tip and the brushes on one or more teeth; and a cover portion on the head tip to provide a shielding protection between the rotating brushes and a cheek, tongue, or lip of a user, thereby preventing discomfort or injury to the user; wherein the head of the mechanical teeth-cleaning device further comprises an opening located in a center portion of the head configured to provide space for dentition as the mechanical teeth-cleaning device is moved and rotated, thereby configured to provide correct positioning of a plurality of bristles generally perpendicular to a long axis of a tooth.

Figure 15:
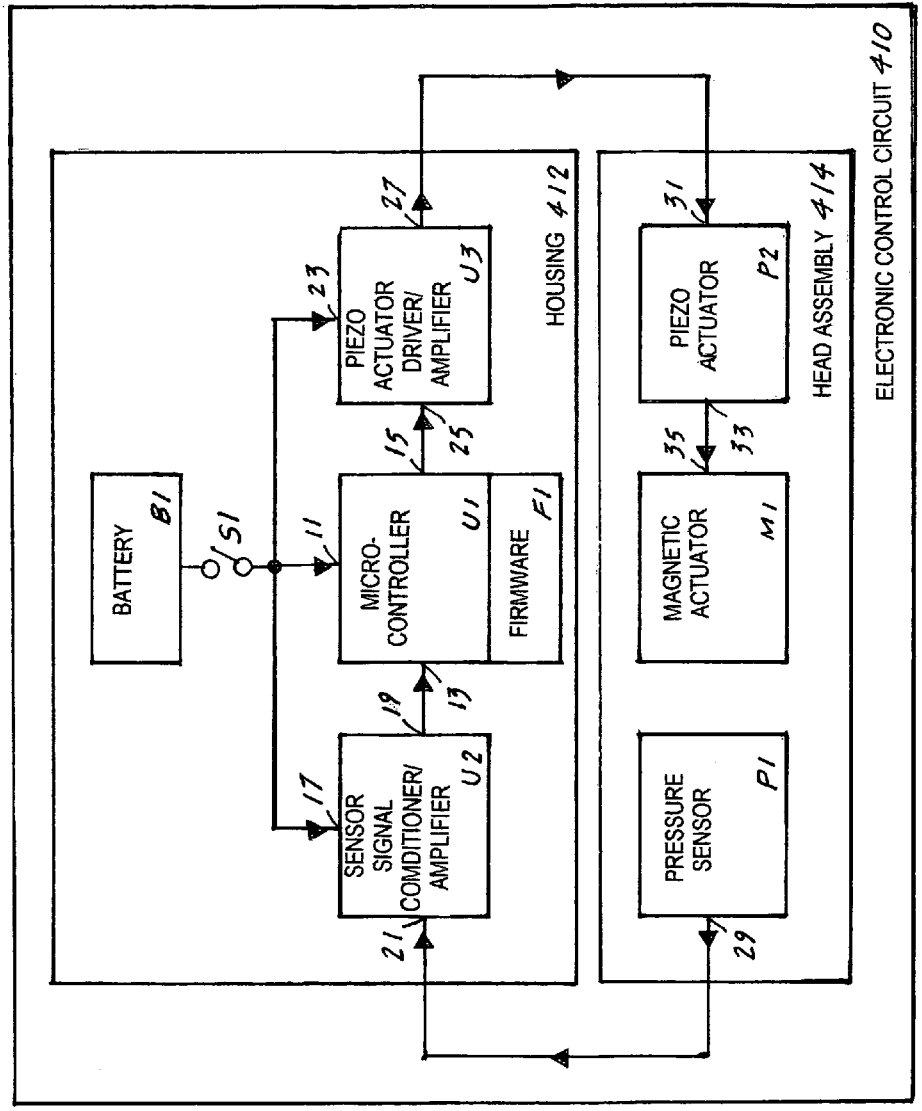
FIG. 15 is a block diagram of the electronic control circuit.

The electric toothbrush features an automatic brush adjusting system (ABAS) that controls the pressure applied to the pair of rotating brushes that interface with the front and the rear sides of a tooth. The preferred embodiment of the ABAS, as shown in FIGS. 15-19, is comprised of an electronic control circuit 410 further comprised of a housing 412 and a head assembly 414, and a flexible brush attachment structure 416. The electronic control circuit 410, as shown in FIG. 15, is comprised of:

A. A power switch S1,

B. A battery B1, which can consist of a rechargeable battery,

C. A microcontroller U1 having a first input 11 connected to the battery B1 via the power switch S1, a second input 13, and a first output 15, D. A sensor signal conditioner/amplifier U2 having a first input 17 connected to the battery B1, an output 19 applied to the second input 13 of microcontroller U1 and an input 21, E. A piezo actuator driver/amplifier U3 having a first input 23 connected to the battery B1, a second input 25 applied from the first output 15 of the microcontroller U1, and an output 27, F. A pressure sensor P1 having an output 29 applied to the input 21 of the amplifier U2, G. A piezo actuator P2 having an input 31 applied from the output 27 of the amplifier U3 and an output 33, and H. A magnetic actuator M1 having an input 35 connected to the output 33 on the piezo actuator P2.

Figure 19:
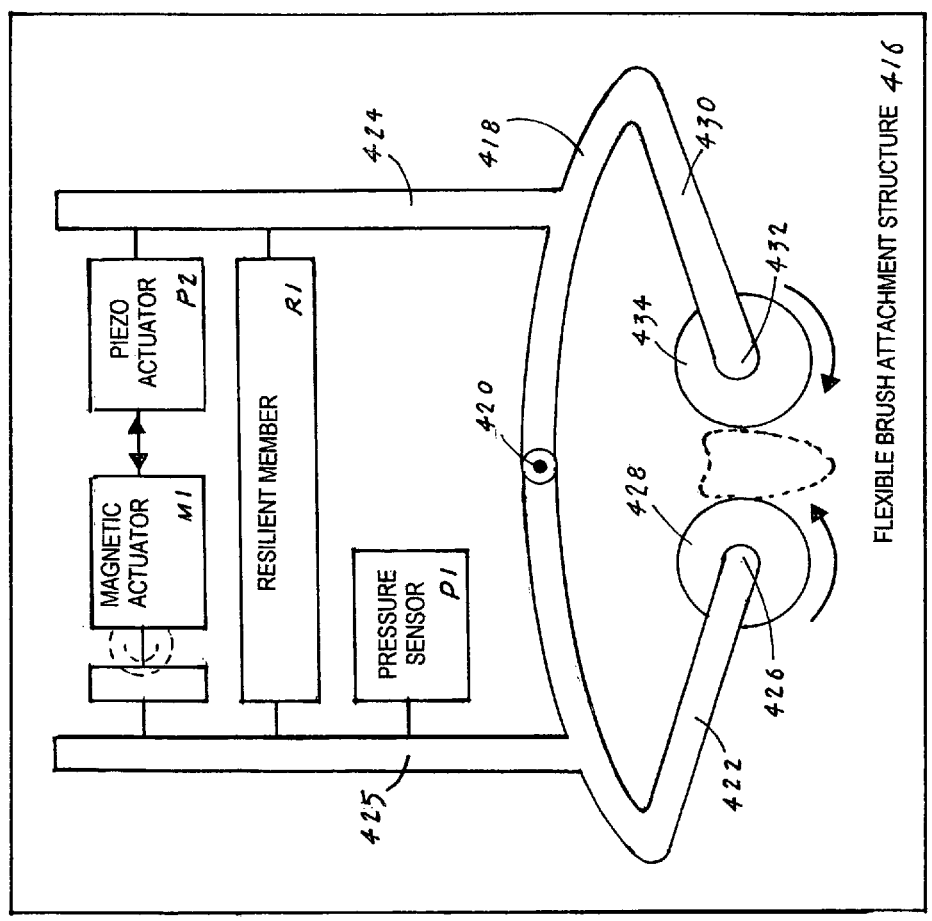
FIG. 19 is a block diagram of a flexible brush attachment structure.

The microcontroller U1, the amplifier U2, the amplifier U3 and the battery B1 are located within the housing 412. The magnetic actuator M1, the pressure sensor P1 and the piezo actuator P2 are located within the head assembly 414 which is an element of the flexible brush attachment structure 416, as shown in FIG. 19.

Figure 17:
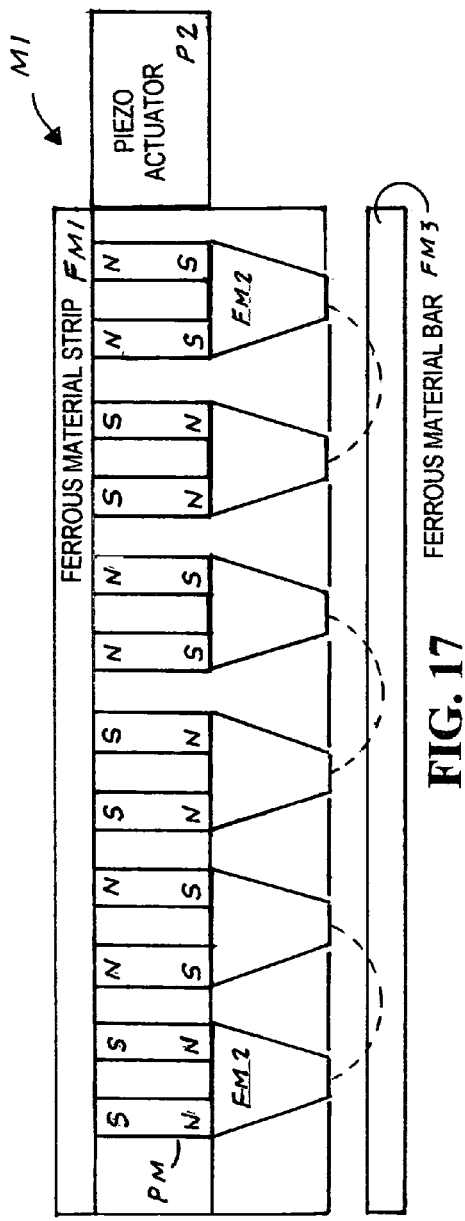
FIG. 17 is an illustration of the magnetic actuator showing an ON state.
Figure 18:
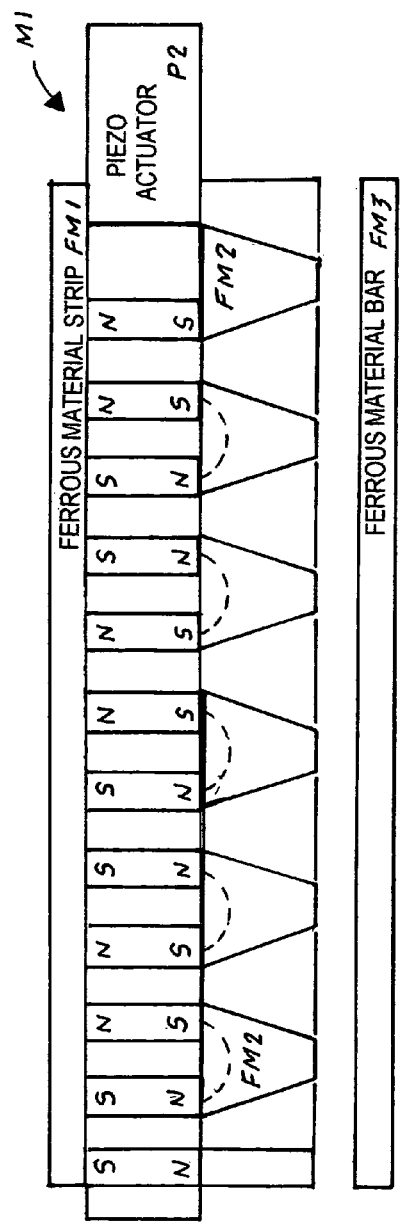
FIG. 18 is an illustration of the magnetic actuator shown in an OFF state.

The magnetic actuator M1, as shown in FIGS. 15, 17, 18 and 19, comprises:

A. A plurality of paired permanent magnets PM having an upper surface and a lower surface, and that are vertically aligned and placed in a series configuration, as shown in FIGS. 17 and 18. At least two permanent magnets are required.

B. A continuous ferrous material strip FM1 that interfaces with and extends across the upper surface of each magnet pair, C. A ferrous material section FM2 that interfaces with the lower surface of each magnet pair, and D. A ferrous material bar FM3 located adjacent and across each section of the ferrous material section FM2.

When power is not applied to the piezo actuator P2, the two north and the two south poles of each magnet pair are aligned with the respective ferrous material section FM2. In this configuration, as shown in FIG. 17, the magnetic actuator M1 is placed in an ON state which causes the two rotating brushes to be pulled inward, thereby increasing the pressure applied to the tooth. Conversely, when power is applied to the piezo actuator P2, the north and south poles shift positions causing a north and a south pole to be aligned with the respective section of the ferrous material. In this configuration, as shown in FIG. 18, the magnetic actuator M1 is placed in an OFF state which causes the two rotating brushes to be pulled outward, thereby decreasing the pressure applied to the tooth.

Figure 16:
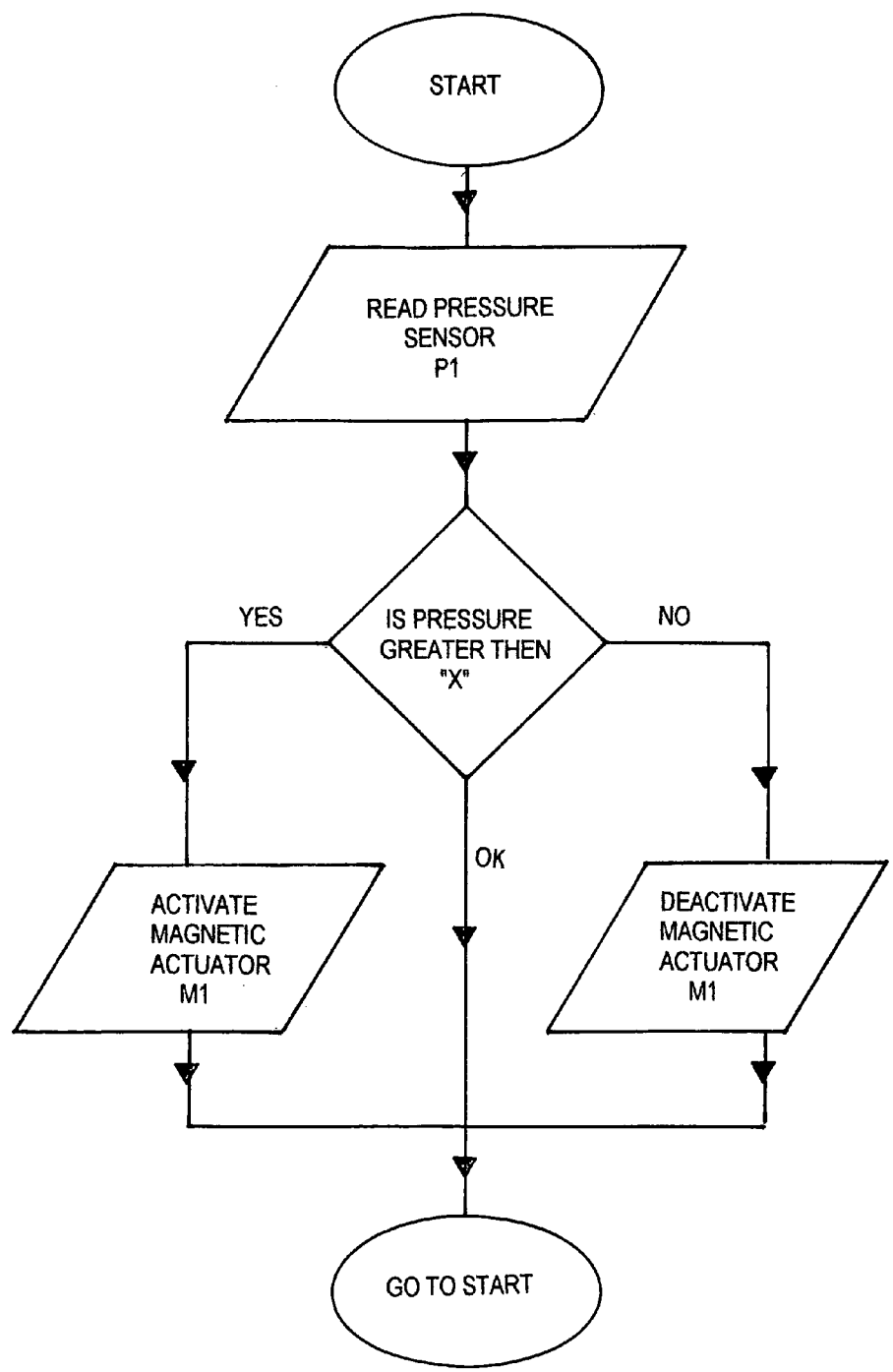
FIG. 16 is a flow diagram of the firmware that operates the microcontroller.

The ON and OFF state of the magnetic actuator M1 is controlled by the microcontroller U1 which, in turn, is controlled by the firmware F1, as shown in FIG. 16. The microcontroller U1 constantly monitors the pressure of the brushes applied against the tooth, via the pressure sensor P1, and continuously adjusts the pressure of the rotating brushes by activating and deactivating the magnetic actuator M1 between its ON and OFF state.

The flexible brush attachment structure 416, as shown in FIG. 19, is comprised of:

A. A curved horizontal section 418 having a centered pivot point 420,

B. A left arm 422 integrally attached to the horizontal section 418 and having a terminus 426 to which is rotatably attached a left brush 428, C. A right arm 430 integrally attached to the opposite side of the horizontal section 418 and having a terminus 432 to which is rotatably attached a right brush 434, D. An upward extending left mounting plate 425 having an outer surface and an inner surface to which is attached the pressure sensor P1 and the ferrous material bar FM3, E. An upward extending right mounting plate 424 having an outer surface and an inner surface to which is attached the piezo actuator P2, which in turn is attached to the magnetic actuator M1 that interfaces with the ferrous material bar FM3, and F. A resilient member R1 that is attached between the inner surface of the left mounting plate 425 and right mounting plate 424, wherein the resilient element R1 maintains the two brushes 428,434 in an outward position, wherein when the electronic control circuit 410 is energized the two brushes are displaced inward about the pivot point 420 to provide pressure on a tooth as controlled by the microcontroller U1.

Operation

The ABAS operates as follows.

The pressure sensor P1 produces a small output voltage that is proportional to the pressure applied by the force between the rotating brushes and the tooth interfacing with the brushes. This voltage is applied to the input of the sensor signal conditioner/amplifier U2 which amplifies the input voltage.

The output of the amplifier U2 is applied to the programmable microcontroller U1 which in combination with the firmware F1 determines how much pressure is being applied between the rotating brushes and the interfacing tooth.

The microcontroller U1 outputs the processed signal to the input of the piezo actuator driver/amplifier U3. The amplifier U3 amplifies the applied signal and produces an output drive voltage that is applied to the piezo actuator P2 that is connected to the magnetic actuator M1. The output drive voltage applied to the piezo actuator P2 causes the permanent magnets in the magnetic actuator M1 to slide forward or backward as controlled by the microcontroller U1.

Power for the entire circuit is provided by a 3-6 volt battery B1 can consists of a single rechargeable battery or comprised of several standard 1.5 volt conventional batteries.

A method for manufacturing a mechanical teeth-cleaning device having two motorized lines of rotating brushes, the method comprising:

utilizing a body defining a user handle;

contouring the body to provide gripability;

configuring the body to contain a miniaturized motor to provide two shafts with counter-rotation and a battery chamber, the body having two protruding and substantially parallel, cylindrical, rotatable shafts mechanically coupled to the motor, configuring the cylindrical, rotatable shafts to provide rotation each in a direction opposite to one another;

utilizing a head secured to the body, configuring the head to connect to the body with a snap-in motion and mechanically coupling the head to the cylindrical, rotatable shafts;

utilizing a head tip containing two, generally parallel, rotating brushes, placing the head tip at the top of the head, each rotating brush being generally cylindrical and each connecting to one of the cylindrical, rotatable shafts, configuring the rotating brushes for simultaneous contact with dentition, one with a buccal side and the other with a lingual side; and separating each rotating brush one from another by a gap of a predetermined width, configuring the gap to correctly accommodate the dentition; and utilizing a guiding stop, locating the guiding stop at a center, underside position of the head tip, configuring the guiding stop to aid a user in obtaining a correct dentition placement position of the head tip and the brushes on one or more teeth.

A method for manufacturing a mechanical teeth-cleaning device having two motorized lines of rotating brushes, the method comprising:

utilizing a body defining a user handle;

contouring the body to provide gripability;

configuring the body to contain a miniaturized motor to provide two shafts with counter-rotation and a battery chamber, the body having two protruding and substantially parallel, cylindrical, rotatable shafts mechanically coupled to the motor, configuring the cylindrical, rotatable shafts to provide rotation each in a direction opposite to one another;

utilizing a head secured to the body, configuring the head to connect to the body with a snap-in motion and mechanically coupling the head to the cylindrical, rotatable shafts;

utilizing a head tip containing two, generally parallel, rotating brushes, placing the head tip at the top of the head, each rotating brush being generally cylindrical and each connecting to one of the cylindrical, rotatable shafts, configuring the rotating brushes for simultaneous contact with dentition, one with a buccal side and the other with a lingual side; and separating each rotating brush one from another by a gap of a predetermined width, configuring the gap to correctly accommodate the dentition;

utilizing a guiding stop, locating the guiding stop at a center, underside position of the head tip, configuring the guiding stop to aid a user in obtaining a correct dentition placement position of the head tip and the brushes on one or more teeth; and utilizing a cover portion on the head tip thereby providing a shielding protection between the rotating brushes and a cheek, tongue, or lip of a user, thereby preventing discomfort or injury to the user, where the head tip is hingedly located at a pivot-point location on an underside of the guiding stop, thereby narrowing the gap between the rotating brushes configured to correctly accommodate the dentition and thereby accommodating any of narrow or front teeth, or where the rotating brushes further comprise bristles of varying lengths and diameters, or wherein the cylindrical, rotatable shafts are comprised of a flexible material to bend as necessary to accommodate varying sizes of teeth.

A method for manufacturing a mechanical teeth-cleaning device having two motorized lines of rotating brushes, the method comprising:
  utilizing a body defining a user handle;
  contouring the body to provide gripability;
  configuring the body to contain a miniaturized motor to provide two shafts with counter-rotation and a battery chamber, the body having two protruding and substantially parallel, cylindrical, rotatable shafts mechanically coupled to the motor, configuring the cylindrical, rotatable shafts to provide rotation each in a direction opposite to one another;
  utilizing a head secured to the body, configuring the head to connect to the body with a snap-in motion and mechanically coupling the head to the cylindrical, rotatable shafts;
  utilizing a head tip containing two, generally parallel, rotating brushes, placing the head tip at the top of the head, each rotating brush being generally cylindrical and each connecting to one of the cylindrical, rotatable shafts, configuring the rotating brushes for simultaneous contact with dentition, one with a buccal side and the other with a lingual side; and separating each rotating brush one from another by a gap of a predetermined width, configuring the gap to correctly accommodate the dentition;
  utilizing a guiding stop, locating the guiding stop at a center, underside position of the head tip, configuring the guiding stop to aid a user in obtaining a correct dentition placement position of the head tip and the brushes on one or more teeth;
  utilizing a cover portion on the head tip, thereby providing a shielding protection between the rotating brushes and a check, tongue, or lip of a user, thereby preventing discomfort or injury to the user;
  utilizing a toggle switch located on the body of the mechanical teeth-cleaning device; and
  configuring the toggle switch to change between two pre-determined width settings, thereby changing a width of the gap configured to correctly accommodate the dentition.

A method for manufacturing a mechanical teeth-cleaning device having two motorized lines of rotating brushes, the method comprising:
  utilizing a body defining a user handle;
  contouring the body to provide gripability;
  configuring the body to contain a miniaturized motor to provide two shafts with counter-rotation and a battery chamber, the body having two protruding and substantially parallel, cylindrical, rotatable shafts mechanically coupled to the motor, configuring the cylindrical, rotatable shafts to provide rotation each in a direction opposite to one another;
  utilizing a head secured to the body, configuring the head to connect to the body with a snap-in motion and mechanically coupling the head to the cylindrical, rotatable shafts;
  utilizing a head tip containing two, generally parallel, rotating brushes, placing the head tip at the top of the head, each rotating brush being generally cylindrical and each connecting to one of the cylindrical, rotatable shafts, configuring the rotating brushes for simultaneous contact with dentition, one with a buccal side and the other with a lingual side; and separating each rotating brush one from another by a gap of a predetermined width, configuring the gap to correctly accommodate the dentition; utilizing a guiding stop, locating the guiding stop at a center, underside position of the head tip, configuring the guiding stop to aid a user in obtaining a correct dentition placement position of the head tip and the brushes on one or more teeth;
  utilizing a cover portion on the head tip, thereby providing a shielding protection between the rotating brushes and a check; tongue, or lip of a user, thereby preventing discomfort or injury to the user;
  utilizing a toggle switch located on the body of the mechanical teeth-cleaning device;
  configuring the toggle switch to change between two pre-determined width settings, thereby changing a width of the gap configured to correctly accommodate the dentition; and
  configuring the toggle switch to switch between two settings, one representing a width of front teeth and one representing a width of back teeth.

A method for manufacturing a mechanical teeth-cleaning device having two motorized lines of rotating brushes, the method comprising:
  utilizing a body defining a user handle;
  contouring the body to provide gripability;
  configuring the body to contain a miniaturized motor to provide two shafts with counter-rotation and a battery chamber, the body having two protruding and substantially parallel, cylindrical, rotatable shafts mechanically coupled to the motor, configuring the cylindrical, rotatable shafts to provide rotation each in a direction opposite to one another;
  utilizing a head secured to the body, configuring the head to connect to the body with a snap-in motion and mechanically coupling the head to the cylindrical, rotatable shafts;
  utilizing a head tip containing two, generally parallel, rotating brushes, placing the head tip at the top of the head, each rotating brush being generally cylindrical and each connecting to one of the cylindrical, rotatable shafts, configuring the rotating brushes for simultaneous contact with dentition, one with a buccal side and the other with a lingual side; and separating each rotating brush one from another by a gap of a predetermined width, configuring the gap to correctly accommodate the dentition;
  utilizing a guiding stop, locating the guiding stop at a center, underside position of the head tip, configuring the guiding stop to aid a user in obtaining a correct dentition placement position of the head tip and the brushes on one or more teeth; and
  configuring the motor of the mechanical teeth-cleaning device to utilize and derive power from both an AC voltage source and a DC voltage source interchangeably, or configuring the two, generally parallel, rotating brushes located in the head tip to rotate in a direction from a gum area upward to a tooth area on a long axis of the tooth to address cleaning an embrasure located between two adjacent teeth and a gum line, and where the rotating brushes are configured to prevent gingival detachment or retrocession, or
  utilizing one or more electrical sensor; and configuring the one or more electrical sensors to automatically detect a width of one or more teeth and to automatically and continually adjust a width of the gap between the rotating brushes configured to correctly accommodate the dentition; or
  configuring the head of the mechanical teeth-cleaning device with an opening located in a center portion of the head configured to provide space for dentition as the mechanical teeth-cleaning device is moved and rotated, thereby configured to provide correct positioning of a plurality of bristles generally perpendicular to a long axis of a tooth.

The foregoing description and drawings comprise illustrative embodiments of the technology described herein. Having thus described exemplary embodiments of the technology described herein, it should be noted by those skilled in the art that the within disclosures are exemplary only, and that various other alternatives, adaptations and modifications may be made within the scope of the technology described herein.

Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing description and the associated drawings. Although specific terms may be employed herein, they are used in a generic and descriptive sense only and not for purposes of limitation. Accordingly, the technology described herein is not limited to the specific embodiments illustrated herein, but is limited only by the claims.

The invention claimed is:

1. A dual rotating electric toothbrush comprising:
   a) a housing having a front end, side walls defining a width of the housing, and a chamber accommodating a power source and a motor;
   b) a head assembly coupled to the front end of the housing, the head assembly comprising:
      (1) first and second elongated mounting members pivotally coupled to each other such that they can pivot about an axis generally parallel to the length of the mounting members;
      (2) a pair of first and second spaced apart shafts extending outwardly from the front end of the housing and through one of the respective mounting members such that they extend beyond an end of the respective mounting member, each of the shafts being rotated by the motor in opposing directions;
      (3) a brush mounted on each of the respective portions of the first and second shafts that extend beyond the mounting members so as to be rotated thereby, each brush having radially outward extending bristles, wherein the other ends of which define a circumferential perimeter, the circumferential perimeter of the bristles of one brush being spaced apart from the circumferential perimeter of the bristles of the other brush by a predetermined distance, and both of the circumferential perimeters being inside the sidewalls defining the width of the housing;
      (4) a protective cover piece extending from the ends of the mounting members and substantially extending over each of the brushes, the cover piece comprised of two portions that are defined by extensions of the respective mounting members which portions of the cover piece are pivoted to each other about an axis generally aligned with the pivot axis of the mounting members, one of the portions of the cover piece including a guide stop located adjacent the pivot axis of the cover pieces which in use is positioned so as to track an upper surface of a tooth located between the brushes, wherein the pivoted mounting members and respective cover pieces constitute a means for automatically moving and adjusting the pressure applied to the pair of spaced apart brushes in response to the width of a particular interfacing tooth located between the brushes, and
   c) means for automatically moving and adjusting the pressure applied to the pair of spaced apart brushes in response to the width of a particular interfacing tooth located between the brushes.

2. The dual rotating electric toothbrush as specified in claim 1 wherein the protective cover piece comprises a hood extending over the brushes.

3. The dual rotating electric toothbrush as specified in claim 1 wherein the combination of the protective cover piece and the sidewalls defining the width of the housing prevent the brushes from contacting surfaces surrounding the toothbrush.

4. The dual rotating electric toothbrush as specified in claim 1 wherein the first and second shafts rotate so that an inner portion of the circumferential perimeter of each of the bristles is rotating upward toward the protective cover piece.

5. The dual rotating electric toothbrush as specified in claim 1 further comprising an arcuate slot formed at the front end of the housing and from which slot the first and second shafts extend.

6. The dual rotating electric toothbrush as specified in claim 1 wherein the sidewalls of the housing define a width which is substantially greater than an outer portion of the circumferential perimeter of the brushes.

7. The dual rotating electric toothbrush as specified in claim 1 wherein the sidewalls of the housing define a width that is essentially twice the distance of the outer portion of the circumferential perimeter of the brushes.

8. The dual rotating electric toothbrush as specified in claim 1 wherein the bristles on the brushes may be of differing lengths.

9. The dual rotating electric toothbrush as specified in claim 1 wherein the shafts are comprised of a flexible material.

10. The dual rotating electric toothbrush as specified in claim 1 wherein the power source is comprised of a battery.

11. The dual rotating electric toothbrush as specified in claim 10 wherein the means for automatically moving and adjusting the pressure applied to the pair of spaced apart brushes in response to the width of a particular interfacing tooth located between the brushes comprises an electronic control circuit comprising:
   a) a power switch (S1)
   b) a battery (B1),
   c) a microcontroller (U1) that functions in combination with firmware (F1), wherein said microcontroller (U1) has a first input (11) connected to the battery (B1) via the power switch (S1), a second input (13), and a first output (15),
   d) a sensor signal conditioner/amplifier (U2) having a first input (17) connected to the battery (B1), an output (19) applied to the second input (13) of the microcontroller (U1) and an input (21),
   e) a piezo actuator driver/amplifier (U3) having a first input (23) connected to the battery (B1), a second input (25) applied from the first output (15) of the microcontroller (U1), and an output (27),
   f) a pressure sensor (P1) having an output (29) applied to the input (21) of the amplifier (U2),
   g) a piezo actuator (P2) having an input (31) applied from the output (27) of the amplifier (U3), and an output (33), and
   h) a magnetic actuator (M1) having an input (35) connected to the output (33) on the piezo actuator (P2).

12. The dual rotating electric toothbrush as specified in claim 11 wherein the microcontroller (U1), the amplifier (U2), the amplifier (U3) and the battery (B1) are located within the housing, and wherein the magnetic actuator (M1), the pressure sensor (P1) and the piezo actuator (P2) are located within the head assembly which is an element of a flexible brush attachment structure comprising:
   a) a curved horizontal section having a centered pivot point,
   b) a left arm integrally attached to the horizontal section and having a terminus to which is rotatably attached a left brush, c) a right arm integrally attached to the opposite side of the horizontal section and having a terminus to which is rotatably attached a right brush, d) an upward extending left mounting plate having an outer surface and an inner surface to which is attached the pressure sensor (P1) and a ferrous material bar (F3), e) an upward extending right mounting plate having an outer surface and an inner surface to which is attached the piezo actuator (P2), which in turn is attached to the magnetic actuator (M1) that interfaces with the ferrous material bar (F3), and f) a resilient member (R1) attached between the inner surfaces of the left and right arms, wherein the resilient member maintains the two brushes in an outward position, wherein when the electronic control circuit is energized the two brushes are displaced inward about the pivot point to provide pressure on a respective tooth as controlled by the microcontroller (U1).

13. The dual rotating electric toothbrush as specified in claim 12 wherein the resilient member is comprised of a compression spring or a leaf spring.

14. The dual rotating electric toothbrush as specified in claim 11 wherein said magnetic actuator (M1) comprises:

a) a plurality of paired permanent magnets with each having an upper surface, a lower surface, and that are vertically aligned and placed in a series configuration, b) a continuous strip of a ferrous material (FM1) that interfaces with and extends across the upper surface of each magnet pair, c) a section of ferrous material (FM2) that interfaces with the lower surface of each magnet pair, and d) a ferrous material bar (FM3) located adjacent and across each section of the ferrous material (FM2), wherein when power is not applied to said piezo actuator (P2), the two north and the two south poles of each magnet pair are aligned with the respective section of the ferrous material which then allows said magnetic actuator (M1) to be placed in an ON state that causes the two rotating brushes to be pulled inward, thereby increasing the pressure applied to the tooth, conversely, when power is applied to said piezo actuator (P2), the north and south poles shift positions causing a north and a south pole to be aligned with the respective section of the ferrous material which then allows said magnetic actuator (M1) to be placed in an OFF state that causes the two rotating brushes to be pulled outward, thereby decreasing the pressure applied to the tooth, wherein the ON and OFF state of said magnetic actuator (M1) is controlled by said microcontroller (U1).

15. The dual rotating electric toothbrush as specified in claim 11 wherein at least two permanent magnets are required.

* * * * *